United States Patent [19]

Schlein

[11] 3,981,308
[45] Sept. 21, 1976

[54] POSITIVE-LOCKING SURGICAL CLAMP

[76] Inventor: Allen P. Schlein, 111 Marconi Ave., Bridgeport, Conn. 06610

[22] Filed: Mar. 3, 1975

[21] Appl. No.: 554,719

[52] U.S. Cl. .............................. 128/346; 81/370; 81/379
[51] Int. Cl.² ...................... A61B 17/00; B25B 7/12
[58] Field of Search ............. 81/367, 368, 369, 370, 81/371, 372, 373, 374, 375, 376, 377, 378, 379, 380; 128/321, 346

[56] References Cited
UNITED STATES PATENTS

| 952,079 | 3/1910 | McIntire | 81/368 X |
|---|---|---|---|
| 2,463,721 | 3/1949 | Spencer, Jr. et al. | 81/379 |
| 2,800,823 | 7/1957 | Tugend | 81/370 |

*Primary Examiner*—Channing L. Pace
*Attorney, Agent, or Firm*—Spencer E. Olson

[57] ABSTRACT

A positive-locking surgical clamp has a first channel-shaped handle provided with a stationary elongated gripping jaw, a movable elongated gripping jaw pivotally mounted on the first handle in cooperative relationship with the stationary jaw and also pivotally joined to one end of a second channel-shaped handle, and a lever disposed within the confronting channels of the two handles and pivotally joined at one end to the second handle and at the other end engaging an adjustably positioned block supported in the channel of the first handle to provide a toggle action which develops a locked grip of large even pressure when the handles are squeezed into engagement with each other. The grip of the clamp is easily released by a thumb-actuated lever disposed alongside one of the handles which operates a cam pivoted within the channel of the handle in a position to engage the lever and force the handles apart.

2 Claims, 4 Drawing Figures

POSITIVE-LOCKING SURGICAL CLAMP

FIELD OF THE INVENTION

This invention relates to surgical clamps, and is more particularly concerned with a positive-locking clamp which a surgeon might use in performing a meniscectomy, for example, to positively grip the meniscus for dissection and removal.

BACKGROUND OF THE INVENTION

Surgical clamps of a wide variety of shapes and sizes, tailored to the surgical procedure for which they are intended, are known and commercailly available. For orthopedic surgery, for example, there are bone clamps of various types, cartilage clamps and meniscus clamps, all of which utilize a box-lock consisting of mating serrations on the confronting surfaces of their scissor-like handles. Although available clamps are generally satisfactory for their intended purpose, it has been found in practice that known meniscus clamps leave much to be desired. While such clamps purport to be self-locking, they do not exert even pressure on the meniscus, particularly when it is necessary for the surgeon to pull on the clamp to withdraw the meniscus from between the knee joint. In so doing with the classical box-lock clamp, the surgeon changes the pressure with which the meniscus is gripped, often resulting in tearing of the meniscal tissue and loss of the grip. this is frustrating to the surgeon because when the clamp comes free, the meniscus tends to recede into the knee joint and has to again be withdrawn and the clamp reset at a different location. Such failures of the clamp of course prolong the operation and also complicates it in terms of wound healing.

SUMMARY OF THE INVENTION

The present invention overcomes these disadvantages of prior art surgical clamps by providing a clamp having a pair of plier-like handles for actuating a pair of elongated gripping jaws and a toggle lever which is brought into action when gripping a meniscus, for example, so as to multiply the pressure of the gripping jaws and positively lock them. One of the jaws is an integral extension of a first of the handles and the second is movable and pivotally connected to the first handle and to the forward end of the other handle. Both handles are of more or less hollow channel or U-shape in cross-section, arranged with their open sides in confronting relationship. A lever within the confronting hollow handles, which normally extends at an angle between the handles, it transversely pivoted at its forward end to the second handle at a point rearwardly of the pivotal connection of the handle and the movable jaw and the other end engages a movable block disposed within the channel of the first handle, the free end of the lever being constrained to a rectilinear path by a transverse pin projecting from both surfaces of the lever which engage aligned longitudinal slots in the channel walls of the first handle. The longitudinal position of the movable block, which determines the jaw spacing when the clamp is closed, is adjustable by a screw longitudinally screwed into the outer end of the handle with its inner end engaging the block. The grip of the clamp is readily released by an eccentric cam transversely pivoted in the channel of the second handle in a position to engage the upper inclined surface of the toggle lever and force the handles apart. The clamp is preferably formed of stainless steel for its non-corrosiveness, durability and amenability to sterilization.

BRIEF DESCRIPTION OF THE DRAWINGS

A better understanding of the construction and operation of the invention will be had from the following description, taken in conjunction with the accompanying drawings, in which.

DESCRIPTION OF THE PREFERRED EMBODIMENT

Figure 7:
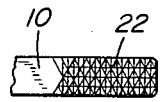
FIG. 7 is a fragmentary view of the gripping surface of one of the jaws of the clamp.
Figure 2:
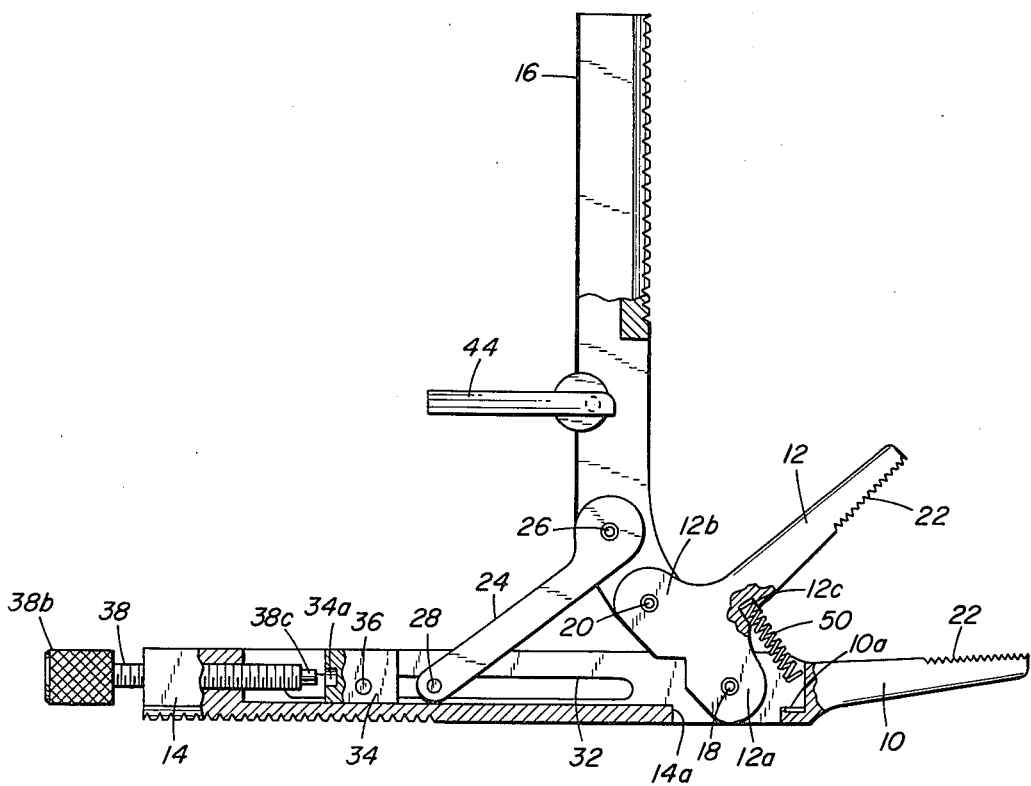
FIG. 2 is a side elevation view of the clamp in its fully open position with portions of the forward sides of the channel-shaped handles broken away to reveal the toggle lever positioned between them.

The clamp according to the invention, all parts which are preferably formed of stainless steel or like non-corrosive metal, comprises a pair of elongated "needle-nose" type jaws 10 and 12, the jaw 10 being an integral extension of one handle 14 of a pair of plier-like handles 14 and 16. Both handles are of more or less hollow channel or U-shape in cross section and are arranged with their open sides in confronting relationship, and when the clamp is closed contact each other throughout substantially their entire length except for that portion of the forward end of handle 16 that curves away from handle 14 to provide a fulcrum for the movable jaw 12. The jaw 12, the elongated portion of which generally conforms in shape and cross section to jaw 10 and arranged to cooperate with jaw 10, is of generally Y-shape with one of its arms 12a transversely pivoted to and between the channel walls of handle 14 at a point 18 near its forward end and with its other arm 12b transversely pivoted to and between the walls of handle 16 at a point 20 near the extremity of its curved forward end. As seen in FIGS. 2, 3, 4 and 6, the bottom of the channel of handle 14 has a cutout at 14a to allow free pivotal movement of the jaw 12 and to facilitate cleaning in the region of the pivot. To insure a firm and positive grip on the work-piece, be it a meniscus or other body tissue, or a surgical pin, the confronting surfaces of the forward ends of jaws 10 and 12 are preferably serrated as at 22 (see FIG. 7) by diamond-shaped teeth formed, for example, by two series of transverse saw cuts at different angles to the longitudinal axis of the jaws.

In order that the surgeon may grip the handle sufficiently firmly to withdraw the tightly held meniscus from between the tibial and femoral portions of the knee, even if his hands are wet, the outer surface of both of handles 14 and 16 have a series of transverse parallel grooves 23 formed therein over approximately half of the length of the handles.

Within the confronting hollow handles is a lever arm 24 which cooperates with handle 16 to form a toggle action. The forward end of lever arm 24 is transversely pivoted to and between the channel walls of handle 16 at a point 26 below and rearwardly of pivot 20, where the handle curves upwardly, and its other end rests on and is free to slide along the bottom of and between the channel walls of handle 14, being constrained to a rectilinear path by a transverse pin 28 projecting from both side surfaces thereof which engage aligned elongated slots 30 and 32 formed in the channel walls. The free end of lever 24 abuts a generally cubical block 34 which is freely slidable within the channel of handle 14, being held therein by a transverse pin 36 projecting from both sides of the block and engaged by the slots 30 and 32. The rearward position of the block 34, and consequently the position of the free end of lever 24, is determined by an adjusting screw 38 longitudinally screwed into the outer end of handle 14, which is made solid as shown for a distance adjacent the end and threaded to receive the screw. The inner end 38a of the screw is received, but not threaded, in a hole 34a in block 34 to provide firm engagement, without side play, between the adjusting screw and the block.

By the construction described the screw 38, which is provided with a knurled head 38b, may be rotated to move the block 34 longitudinally to set the position of the block and thereby adjust the spacing of the jaws for the thickness of the object 40, such as the meniscus of the knee, to be gripped, and when the jaws are closed upon the object by squeezing the handles towards one another, the toggle lever 24 will straighten out through a line 42 drawn through the centers of pivot pins 20 and 26 and the point of engagement of the free end of lever 24 with block 34, to thereby develop an enormous pressure on the grip. The location of pivot 26 relative to pivot 20 and the length of lever 24 are such as to permit the center of pivot pin 26 to just pass the line 42 when the handles are closed and in contact with each other so as to lock the grip on the object to thereby avoid the otherwise necessity of applying hand pressure on the handles all the time. Significantly, when the clamp is in its closed position application of additional hand pressure to the handles, as would occur when the clamp is pulled to withdraw the meniscus for dissection, does not affect the pre-adjusted spacing of the gripping jaws; thus, the gripping pressure remains essentially constant and minimizes the possibility of tearing of tissue and loss of the grip as frequently occurs with prior art clamps. The described clamp has a range of adjustment of jaw spacing from essentially zero to about one-quarter inch.

Figure 1:
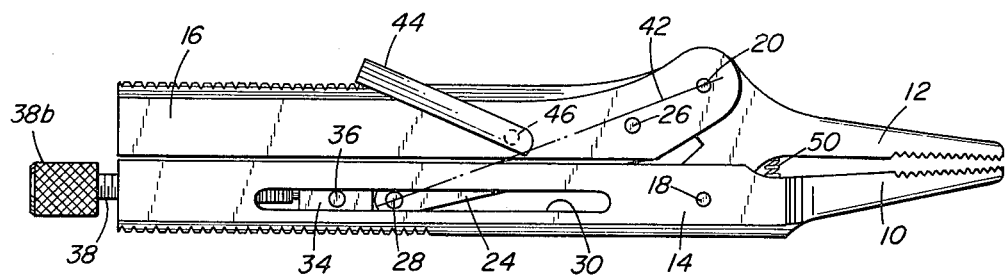
FIG. 1 is a side elevation view, in actual size, of the clamp in its closed position.
Figure 3:
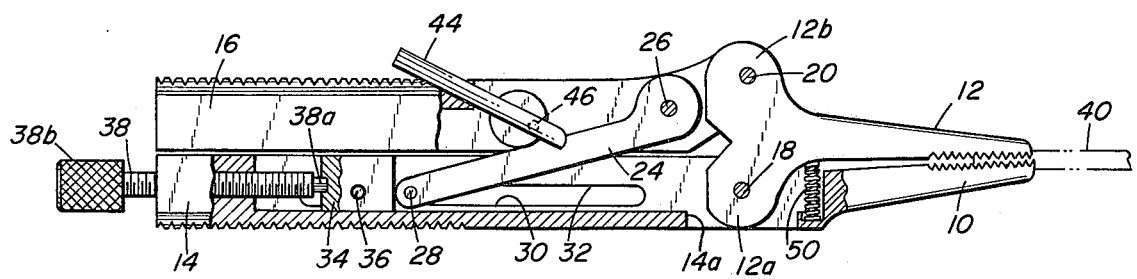
FIGS. 3 and 4 are side elevation views of the clamp in closed and partially open positions, respectively, with portions of the forward sides of the channel-shaped handles broken away to reveal the releasing cam positioned between them.
Figure 4:
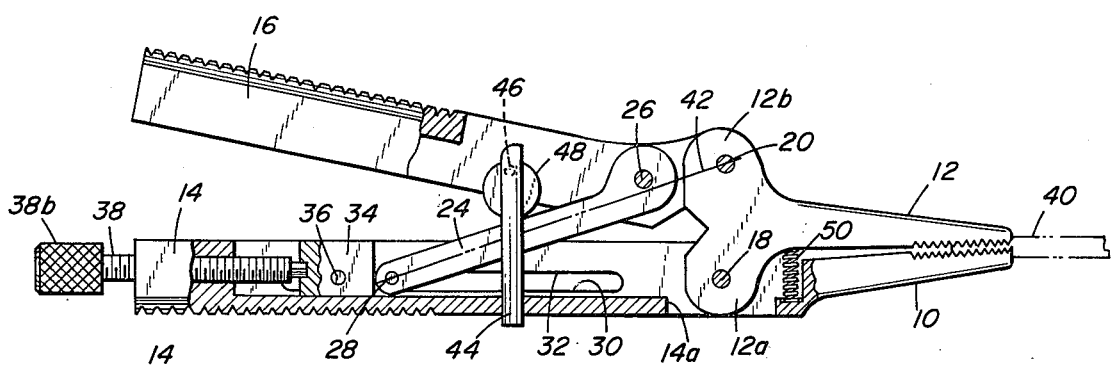
Figure 5:
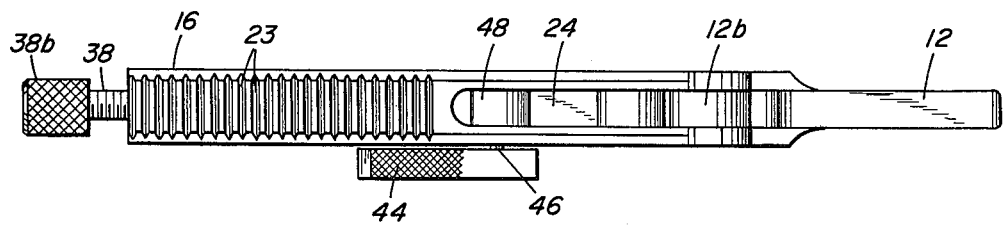
FIG. 5 is a top plan view of FIG. 1.
Figure 6:
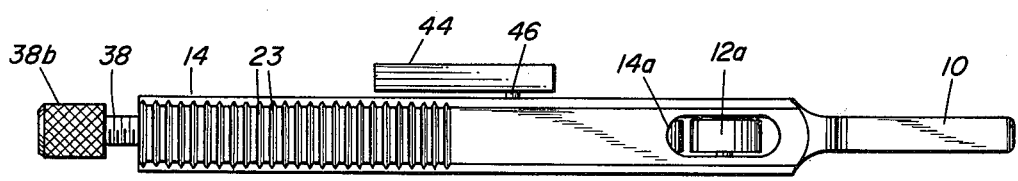
FIG. 6 is a bottom plan view of FIG. 1.

When the operation being performed is finished, the locked toggle grip may be easily released by pressing downward, as with the thumb, on a small release lever 44 disposed closely parallel alongside one outside wall of handle 16 and secured near one end thereof to a pin 46 transversely pivoted on the channel walls. Disposed within the channel of handle 16 is a circular disk 48 eccentrically secured to the pin 46, the pin being offset from the center of the disk and the disk having a diameter such when the clamp is closed (as best seen in FIG. 3) the disk tangentially engages the outer inclined surface of lever 24, with the release lever 44 being inclined upwardly and rearwardly. As the free end of lever 44 is pressed downwardly to cause rotation of pin 46, the attendant rotation of the eccentric disk 48 results in a camming action between the disk and lever 24 to forcibly move handle 16 away from handle 14 to carry the center of pin 26 back over the center line 42 (as best seen in FIG. 4) so that the toggle will collapse and the clamp will at once open. The pin is located relative to the bottom of the channel in handle 16 and the diameter of the disk is such that when lever arm 44 is rotated clockwise (as viewed in FIG. 1, for example) the disk engages the bottom of the channel to preclude rotation beyond the point at which lever arm 44 will still be inclined upwardly and rearwardly.

Opening of the jaws is assisted by a helical compression spring 50 disposed between the jaws 10 and 12, inwardly from the serrated gripping surfaces, being secured at one end by being press fit into a cylindrical recess 12c in the jaw 12 with the other end constrained by a transverse wall and a transverse shelf 12a at the forward end of the channel of the handle 16. The spring 50 is relatively soft so as to gradually force the jaws apart when the toggle is released by release lever 44, unaccompanied by any violent snap-action type of opening as might cause the user to lose his grip on the handles or damage the tissue being gripped.

The above-described embodiment of the invention is intended to be merely exemplary, and numerous variations and modifications may be made by those skilled in the art without departing from the spirit and scope of the invention. For example, the release lever 44 could as well be disposed on the opposite side of handle 16 from that shown, and the disk 48 need not necessarily be circular, the only requirement being that it has a shape in the region thereof that engages lever arm 24 to force the handles apart, when the release arm is rotated, sufficiently to release the toggle. All such variations and modifications are intended to be included within the scope of the invention as defined in the appended claims.

I claim:

1. A surgical clamp comprising, in combination:
a first substantially straight channel-shaped handle of U-shape cross-section having an open side and forward and rearward ends and having an integral elongated stationary jaw extending substantially co-linearly from the forward end thereof,
a second channel-shaped handle of U-shape cross-section having an open side and forward and rearward ends disposed with its open side in confronting relationship with the open side of said first handle, said second handle being substantially straight throughout a major portion of its length and having its forward end curved away from the first handle,
a movable elongated jaw disposed between and transversely pivoted to the channel walls at the forward end of said first handle rearwardly of said stationary jaw and disposed within and transversely pivoted to the channel walls of the second handle near the extremity of its curved forward end and arranged to cooperate with the stationary jaw to grip an article,
an overcenter locking element comprising a lever having a forward end transversely pivoted to and between the channel walls of the second handle at a point rearwardly of the pivotal connection thereof with the movable jaw and inclined rearwardly with its other end engaging a block member slidably supported within the channel of the first handle, said block member having pins extending transversely therefrom and engaging longitudinal slots formed in the channel walls and being longitudinally adjustable by an adjusting screw threaded into the rearward end of the first handle, said locking element being arranged to lock the clamp when the handles are squeezed by hand into contact with each other, and means for releasing the clamp comprising a disk eccentrically pivoted to and between the channel walls of said second handle by a transverse pivot pin, said disk being secured to said transverse pivot pin, and a release lever secured to said transverse pivot pin and disposed closely parallel along and outside one of the channel walls of the second channel, said disk being engageable with the surface of the locking element lever that confronts the second handle and operative upon rotation of said release lever and said transverse pivot pin to impart a releasing movement to said locking element.

2. A surgical clamp in accordance with claim 1, further including compression spring means disposed between said stationary and movable jaws, said compression spring means being secured at one end to said movable jaw with its other end engaging said stationary jaw so as to be compressed when the clamp is locked and to force said jaws apart upon release of the locking element.

* * * * *